United States Patent
Cadenhouse-Beaty

(10) Patent No.: US 10,557,090 B2
(45) Date of Patent: Feb. 11, 2020

(54) PROCESS FOR PRODUCING TRANSPORT FUEL BLENDSTOCK

(71) Applicant: Patrick James Cadenhouse-Beaty, Milton Keynes (GB)

(72) Inventor: Patrick James Cadenhouse-Beaty, Milton Keynes (GB)

(73) Assignee: Patrick James Cadenhouse-Beaty, Milton Keynes (GB)

( * ) Notice: Subject to any disclaimer, the term of this patent is extended or adjusted under 35 U.S.C. 154(b) by 0 days.

(21) Appl. No.: 15/844,210

(22) Filed: Dec. 15, 2017

(65) Prior Publication Data

US 2018/0127665 A1 May 10, 2018

Related U.S. Application Data

(63) Continuation of application No. PCT/AU2016/050526, filed on Jun. 22, 2016.

(30) Foreign Application Priority Data

Jun. 22, 2015 (AU) .................. 2015902392

(51) Int. Cl.
*C07C 2/08* (2006.01)
*C10G 61/08* (2006.01)
(Continued)

(52) U.S. Cl.
CPC ............ *C10G 61/08* (2013.01); *C10L 1/06* (2013.01); *C10G 2300/1081* (2013.01);
(Continued)

(58) Field of Classification Search
CPC ........ C10G 61/08; C10G 35/04; C10G 50/00; C10G 57/005; C10G 57/02; C10G 11/06;
(Continued)

(56) References Cited

U.S. PATENT DOCUMENTS 2,276,171 A * 3/1942 Bartlett ................ C10G 29/205
208/64
2,377,579 A * 6/1945 Schulze .................. C07C 11/12
585/616

(Continued)

FOREIGN PATENT DOCUMENTS

WO     03012011 A1   2/2003
WO  2006094010 A2   9/2006

(Continued)

OTHER PUBLICATIONS

International Search Report, dated Jun. 22, 2015, for International Patent Application PCT/AU2016/050526, 6 pages.

(Continued)

*Primary Examiner* — Huy Tram Nguyen
(74) *Attorney, Agent, or Firm* — Kilpatrick Townsend & Stockton LLP

(57) ABSTRACT

A process for producing transport fuel blendstocks comprises providing a first feedstock comprising butane and propane and a second feedstock comprising benzene and dehydrogenating the first feedstock in a first reactor to produce a C4 product comprising butane and butene and a C3 product comprising propane and propylene. The process also comprises oligomerizing the C4 product in a second reactor to produce a first transport fuel blendstock and alkylating the C3 product with the second feedstock in a third reactor to produce a second transport fuel blendstock.

15 Claims, 3 Drawing Sheets

(51) Int. Cl.
*C10G 57/02* (2006.01)
*C10L 1/06* (2006.01)

(52) U.S. Cl.
CPC ............ *C10G 2300/305* (2013.01); *C10G 2300/4056* (2013.01); *C10G 2400/02* (2013.01); *C10L 2200/0423* (2013.01); *C10L 2270/023* (2013.01); *C10L 2270/10* (2013.01); *C10L 2290/56* (2013.01)

(58) Field of Classification Search
CPC .... C07C 2/08; C07C 5/32; C07C 5/48; C01G 29/205
USPC .......................................... 422/630
See application file for complete search history.

(56) References Cited

U.S. PATENT DOCUMENTS

| | | | |
|---|---|---|---|
| 2,526,966 A | 10/1950 | Oberfell et al. | |
| 2,848,514 A * | 8/1958 | De Keizer | C07C 2/66 585/302 |
| 4,275,255 A | 6/1981 | Vora | |
| 4,482,772 A | 11/1984 | Taback | |
| 4,675,461 A | 6/1987 | Owen et al. | |
| 4,678,645 A | 7/1987 | Chang et al. | |
| 5,055,627 A | 10/1991 | Smith, Jr. et al. | |
| 5,252,197 A | 10/1993 | Alexander et al. | |
| 5,955,641 A * | 9/1999 | Chen | C07C 2/66 208/135 |
| 6,025,533 A | 2/2000 | Vora et al. | |
| 6,111,159 A | 8/2000 | Huff et al. | |
| 6,888,037 B2 | 5/2005 | Dandekar et al. | |
| 2002/0016520 A1 | 2/2002 | Paggini et al. | |
| 2010/0145118 A1* | 6/2010 | Zimmerman | C07C 7/163 585/258 |
| 2015/0159099 A1 | 6/2015 | Luebke et al. | |

FOREIGN PATENT DOCUMENTS

| | | |
|---|---|---|
| WO | 2009055227 A1 | 4/2009 |
| WO | 2011120968 A2 | 10/2011 |

OTHER PUBLICATIONS

Written Opinion, dated Jun. 22, 2015, for International Patent Application PCT/AU2016/050526, 5 pages.
Gussow, S. et al. "Dehydrogenation links LPG to more octanes", *Oil & Gas Journal*, Dec. 8, 1980 (1980), Abstract Only, 1 page.
Extended European Search Report dated Oct. 12, 2018 in EP Patent Application No. 16813386.6. 12 pages.
Stockle, Mike et al.; "Dealing with dieselisation"; Internet Citation; Nov. 11, 2009; XP002587070; Retrieved from internet: <URL: http://www.fwc.com/publications/tech_papers/files/Dealing%20with%20dieselisation%20ERTC%202009.pdf>; retrieved on Jun. 11, 2010; pp. 1-15.

* cited by examiner

US 10,557,090 B2

PROCESS FOR PRODUCING TRANSPORT FUEL BLENDSTOCK

CROSS-REFERENCES TO RELATED APPLICATIONS

This application is a continuation application of International Patent Application No. PCT/AU2016/050526 entitled "PROCESS FOR PRODUCING TRANSPORT FUEL BLENDSTOCK," filed on Jun. 22, 2016, which claims priority to Australian Patent Application No. 2015902392, filed on Jun. 22, 2015, which are herein incorporated by reference in their entirety for all purposes.

TECHNICAL FIELD

The present invention relates to processes and systems (referred to herein as a "process arrangement") for producing transport fuel blendstocks, in particular for producing high octane gasoline fuel.

BACKGROUND

One prior art oil industry process arrangement for producing transport fuel blendstocks, as previously conceived (and manifested in the design of many oil refineries worldwide), comprises a conventional refining flowscheme consisting of (separate and discrete) Crude Oil or Condensate Distillation, Saturates Gas Processing, Naphtha Pre-treatment, Continuous or Semi-regenerative Catalytic Reforming (CCR or PtR), and Kerosene Hydrotreating and Diesel Hydroprocessing plants. This process arrangement results in an operation where the benzene and aromatics contents of the resulting product motor gasoline pool can only be kept below the applicable specification maxima of 1% and 45% respectively at a low average pool RONC of around 92.5.

Supplementation of the gasoline pool by addition of high aromatics content (93-95 RONC) FCC (Fluid Catalytic Cracker) naphthas—even blended with high octane zero aromatics content (95-98 RONC) alkylates—does not materially alter the picture, as FCC naphthas also contain high quantities of benzene and other aromatics. Accordingly, approximately ½ to ⅔ of gasoline production of many existing oil refineries is low-octane 91R grade, unsuitable for modern motor vehicle engines (which require a minimum 95RONC), and which would in future have to be sold at lower export refinery gate "netback" prices into the lower product quality markets. Oil refineries also co-produce significant quantities of low value LPG, which can compete with surplus export by-product LPG from natural gas and LNG production.

Adding a Naphtha Splitter and Light Naphtha Isomerisation unit, the "traditional" refining industry naphtha isomerisation route to gasoline pool benzene and aromatics content reduction, achieves little, as it results in a process arrangement still barely able to satisfy even a 50/50% 95/91R gasoline grade pool demand, as gasoline benzene and aromatics content reach their respective specification maxima at an overall gasoline pool octane of around 93.5RONC.

Installation of a benzene saturation unit ("BenSat") both consumes additional valuable hydrogen and simultaneously reduces pool octane by converting 100RONC benzene to 67RONC cyclohexane, which then has to be made up by a markedly higher severity CCR operation. The combined effect is to increase plant capital expenditure and decrease liquid yield, thus further reducing profitability. This effect is clearly demonstrated in the recent and impending closure of refineries worldwide with such antiquated processing schemes.

Typically in the oil refining and petrochemical manufacturing industry, process units are designed to manufacture products of a sufficiently high purity to meet a specified design quality standard. This usually results in the prior art process arrangements described being comprised of discrete process units, all with their own stand-alone primary reaction sections and secondary product purification facilities. These normally consist of fractionation columns and associated vessels, heat exchangers, pumps, valves and piping, and constitute significant capital investment, often comprising 50% or more of the Total Installed Cost (TIC) of the process unit.

The above description is not to be taken as an admission of the common general knowledge.

BRIEF SUMMARY

According to the present invention there is provided a process for producing transport fuel blendstocks, the process comprising:

providing a first feedstock comprising butane and propane, and a second feedstock comprising benzene;

dehydrogenating the first feedstock in a first reactor to produce a C4 product comprising butane and butene and a C3 product comprising propane and propylene;

oligomerizing the C4 product in a second reactor to produce a first transport fuel blendstock; and alkylating the C3 product with the second feedstock in a third reactor to produce a second transport fuel blendstock.

The first feedstock may contain at least 80 vol. % butane and propane.

The first feedstock may contain at least 95 vol. % butane and propane.

The second feedstock may contain at least 50 vol. % benzene.

The second feedstock may contain at least 60 vol. % benzene.

The C4 product may contain at least 80 vol. % butane and butene.

The C4 product may contain at least 95 vol. % butane and butene.

The C3 product may contain at least 80 vol. % propane and propylene.

The C3 product may contain at least 95 vol. % propane and propylene.

The process may comprise splitting the C4 product from the C3 product that is produced in the first reactor.

The process may comprise recovering butane from an output of the second reactor and transferring the butane to the first reactor.

The process may comprise recovering propane from an output of the third reactor and transferring the propane to the first reactor.

The process may comprise obtaining the second feedstock from catalytically reformed naphtha.

The process may comprise obtaining the second feedstock as a benzene rich side stream from the stabilizer column of a catalytically reformed naphtha process unit.

The process may comprise recovering any one or more of propane, propylene or benzene from the output of the third reactor and transferring the propane, propylene and/or benzene to the stabilizer column of the catalytically reformed naphtha process unit.

The process may comprise recovering the propane and propylene in an output from the above stabilizer column and transferring the recovered propane and propylene to the first reactor.

The process may comprise outputting a third transport fuel blendstock from the stabilizer column for blending on site.

The process may comprise returning all of the output of the third reactor to the stabilizer column of the naphtha reforming process unit.

The invention also provides a system for producing transport fuel blendstocks, the system comprising:

a first reactor for dehydrogenating a first feedstock comprising butane and propane to produce a C4 product comprising butane and butene and a C3 product comprising propane and propylene;

a second reactor for oligomerizing the C4 product in a second reactor to produce a first transport fuel blendstock; and a third reactor for alkylating the C3 product with a second feedstock comprising benzene in a third reactor to produce a second transport fuel blendstock.

The first feedstock may contain at least 80 vol. % butane and propane.

The first feedstock may contain at least 95 vol. % butane and propane.

The second feedstock may contain at least 50 vol. % benzene.

The second feedstock may contain at least 60 vol. % benzene.

The C4 product may contain at least 80 vol. % butane and butene.

The C4 product may contain at least 95 vol. % butane and butene.

The C3 product may contain at least 80 vol. % propane and propylene.

The C3 product may contain at least 95 vol. % propane and propylene.

The system may comprise a separator for recovering butane from an output of the second reactor and transferring the butane to the first reactor.

The system may comprise a C3/C4 splitter for splitting the C4 product from the C3 product that is produced in the first reactor.

The system may comprise modification to a stabilizer column of a catalytically reformed naphtha process unit to produce the second feedstock as a benzene rich side stream.

The system may comprise a separator for recovering any one or more of propane, propylene or benzene from an output of the third reactor and transferring the propane, propylene and/or benzene to the stabilizer column.

The invention also provides a transport fuel comprising a blendstock produced by the process as described above or using the system as described above.

The above-described process arrangement of the invention provides an opportunity for capital and operating cost savings and significant margin increase via upgrading refinery-produced and/or purchased LPG to gasoline.

Integration of the dehydrogenation plant with the oligomerisation and alkylation plants provides an opportunity for removing the need for costly separation of propane from propylene and butane from the butenes, as the entire butane/butenes C4 product from the dehydrogenation plant is fed directly to the oligomerisation unit, and the entire propane/propylene C3 product from the dehydrogenation plant is fed directly to the benzene alkylation unit.

The equipment required in the dehydrogenation section of the new process arrangement is a process heater, a dehydrogenation reactor and associated heat recovery equipment, followed by hydrogen recovery and a simple C3/C4 splitter.

Traditionally, the co-dehydrogenation of propane and butanes would require all of the above equipment, plus a propylene/propane (C3) splitter to enable recycle of unreacted propane back to the front end of the process, and a butenes/butanes (C4) splitter to enable recycle of unreacted butanes, also back to the front end of the process unit. Relatively pure streams of propylene and butenes would be produced.

The oligomerisation section of both the new process arrangement of the invention and the traditional process arrangement described in the Background section of the specification consists of a process heater, an oligomerisation reactor and associated heat recovery equipment, followed by an oligomer product stabiliser. The overhead product from the stabiliser contains mainly butanes, along with a small amount of unreacted butenes, which "butane-rich" stream is recycled back to the front end of the dehydrogenation section.

The alkylation section of the process arrangement of the invention comprises an alkylation reactor, followed by a simple alkylate product stabiliser. The alkylation reactor receives the mixed propylene/propane product stream from the dehydrogenation section of the new process arrangement, together with a benzene-rich sidestream taken from the catalytic reformer product stabiliser. As the reaction between benzene and propylene takes place at low temperatures, no significant heat input or heat recovery equipment is required. The overhead product from the alkylate stabiliser contains mainly propane, along with a small amount of unreacted propylene and unreacted benzene, which stream is recycled back to the catalytic reformer product stabiliser feed for recycle of unreacted benzene and recovery of propane. The propane is recovered as part of the overhead product of the catalytic reformer product stabiliser, together with propane and butanes produced in the catalytic reformer, and is routed to the feed stream of the dehydrogenation plant.

The alkylate recovered as the bottom product of the alkylate stabiliser may be either blended directly into the stabilised catalytic reformer product within battery limits, or may be routed separately to storage if there is benefit to the refiner in isolating this very high octane gasoline blendstock, e.g. for manufacture of high octane aviation gasoline.

Traditionally, alkylation of benzene in catalytic reformer product requires splitting of this "reformate" stream into a light reformate and a heavy reformate, followed by alkylation with propylene in a separate stand-alone process unit.

In the process arrangement of the invention, the omission of the propylene/propane (C3) splitter and the butenes/butanes (C4) splitter and the reformate splitter and their associated overhead vessels, heat exchangers, pumps, piping and instrumentation provides an opportunity for a considerable saving in both plant capital expenditure and ongoing operating costs. These are three large and complex distillation towers: the C3 splitter needs some 95 distillation trays to separate propylene from propane, the C4 splitter around 55 trays to separate butenes from butanes, and the reformate splitter is a very high energy consumer.

If the LPG is purchased, it is preferably mixed butanes, as (a) this is cheaper than a mixture of propane and butanes and (b) there is sufficient propane in both crude oil and/or condensate, and produced by the refinery's catalytic reformer, to provide enough propylene to alkylate virtually all the benzene contained in the reformer product.

The invention may include inter-unit integration of the refinery's Saturates Gas Plant (SGP) with the Paraffins Dehydrogenation plant and the Olefins Oligomerization unit. The Benzene Alkylation plant reaction section may also be highly integrated with the CCR product stabilizer operation.

The process arrangement of the invention provides an opportunity for collectively optimizing the conversion of LPG (that produced within the plant, together with imported purchased LPG, preferably predominantly mixed butanes, and preferably predominantly isobutane) to high octane gasoline, and—via process simplification and a high degree of integration—simultaneously and collectively result in significant TIC (Total Installed Cost) and operating cost savings by enabling the omission of equipment items used in the unnecessary purification of process unit products. The combination of conversion of otherwise exported low value LPG into a high value high octane isooctene-rich 100RONC gasoline blending component via integrated butane dehydrogenation (BDH) and downstream butane oligomerisation (PN)—and simultaneous co-conversion of produced propane to propylene enabling the alkylation of a 100RONC benzene-rich CCR product heartcut to a 118RONC cumene-rich blendstock—together provide an opportunity for boosting the gasoline pool octane substantially, potentially enabling a high proportion of high octane 98R Super and 95P Premium grades to be manufactured (exceeding 80% of gasoline production), while maintaining the same—or reducing—CCR severity. Gasoline aromatics may now be below specification limits at a pool octane of 95.3, with 94RONC CCR reformate comprising under 64% of the motor gasoline pool.

The process arrangement of the invention additionally provides an opportunity for achieving a maximum overall plant liquid yield and increased production volume, while minimizing plant fuel use and CO2 emissions, all of which impact favourably on plant economics.

In this context, increasing the BDH and PN plant capacities to enable the import and conversion of additional butanes into iso-octenes may prove economically attractive; this option could be limited by individual gasoline grade olefins specification maxima.

The process arrangement of the invention provides an opportunity for taking oil refinery, or condensate processing plant, butane-rich light paraffinic streams, preferably containing high proportions of isobutane, and converts them into butenes via dehydrogenation (via competing process licensor processes) for utilization in conjunction with an integrated downstream oligomerization process (such as Axens' "Polynaphta" or UOP's "InAlk" catalytic oligomerization, or competing third party processes), to produce a high octane low aromatic content oligomer gasoline blendstock.

The process arrangement of the invention provides an opportunity for producing propylene, via the co-dehydrogenation of refinery propane, for downstream utilization in a benzene alkylation process to beneficially remove benzene from the refinery gasoline pool via conversion of benzene to higher octane cumene. Propylene can also be used in the above oligomerization process, but the octane number of oligomer gasoline made from propylene is lower than that made from butenes.

If warranted, n-butane may be isomerized into isobutane prior to dehydrogenation. This may further increase the RONC of the resulting oligomer, and can be achieved by incremental co-isomerization of butane with pentane in an isomerization unit (such as Axens' or UOP's light paraffins isomerization process technology), or by isomerization of n-butane in a dedicated process unit.

The above, taken together, provides an opportunity for an oil refinery or condensate processing plant to minimize the severity at which its catalytic reforming process unit operates, thereby increasing the plant's overall liquid yield. This translates into higher plant profitability (increased manufacturing margin) by maximizing the quantity of liquid transport fuels products, while minimizing the amount of lower value LPG and gases produced.

A high level of inter-unit integration provides an opportunity for minimising the capital and operating costs of the process arrangement.

The process arrangement of the invention provides an opportunity for minimizing the Total Installed Capital (TIC) cost and the ongoing Operating Cash Cost of Production (CCOP) of facilities to manufacture high quality transport fuels from petroleum condensate, thereby providing an opportunity for maximizing the profitability (manufacturing margin) achieved by such facilities.

The installation of a light paraffins dehydrogenation process in conjunction with (and highly integrated with) a downstream oligomerization process to manufacture high octane low aromatics content oligomer gasoline blendstocks, provides an opportunity for reducing catalytic reforming (CCR or PtR) process plant severity, increasing overall high value liquid yield, and decreasing lower value LPG and gas production.

The integration of the above light paraffin dehydrogenation and oligomerization processes with each other—and with the other processing units of the plant—provides an opportunity for reducing both TIC and Operating costs via process simplification, resulting in the avoidance of the need for separate butane and butenes separation (i.e. investment in and operation of a C4 splitter). Intensive integration of these two processes results in the consumption of the olefins—which are reactive in the downstream oligomerization process—from the combined inert paraffin and reactive olefin product of the upstream dehydrogenation process, leaving a more concentrated paraffin stream for recycle back to the upstream unit, where it is converted into olefin. Normal butane (n-butane) and isobutane are inert diluents in the oligomerization process, so this integration of oligomerization unit with the light paraffins dehydrogenation unit provides an opportunity for avoiding the need for separate n-butane/isobutane and butene/isobutene separation in the light paraffins dehydrogenation plant; accordingly the attendant investment in, and operation of, olefins purification facilities in this unit are thus obviated.

The isomerization of n-butane to isobutane prior to dehydrogenation in an Isomerization Unit (ISOM) may be used to further increase the Clear Research Octane Number (RONC) of oligomer produced, again reducing catalytic reforming process plant severity, and further increasing overall plant high value liquid yield and decreasing lower value LPG and gas production. This butane isomerization may take place as co-isomerization of butane with pentane in a combined butane-pentane isomerization unit to realize additional capital expenditure savings.

The introduction of a benzene alkylation process provides an opportunity for reducing gasoline benzene levels to meet specification in the most economically beneficial fashion, by alkylation of 100RONC benzene to 118RONC cumene.

The integration of the above benzene alkylation process with the catalytic reforming process unit (CCR or PtR)

provides an opportunity for reducing both TIC and Operating costs via process simplification. A benzene-rich sidedraw is taken from the CCR (or PtR) product stabilizer and passed through the benzene alkylation process reactor, where it is alkylated with a propylene-rich C3 product stream (from the paraffin dehydrogenation plant) over a zeolite-based or other catalyst and where all propylene is consumed. The reactor products are returned to the upper section of the CCR (or PtR) stabilizer column, where unreacted excess benzene is recovered for recycle, propane is returned as recycle back to the light paraffins dehydrogenation plant and cumene leaves the stabilizer mixed with the bottom "reformate" product. Propane is inert in the benzene alkylation process, so this integration of benzene alkylation unit with the light paraffins dehydrogenation unit avoids the need for separate propane and propylene separation in the light paraffins dehydrogenation plant, and the attendant investment in and operation of a C3 splitter may thus be obviated.

The process arrangement of the invention may include a light paraffins dehydrogenation process to be utilized in conjunction with an integrated downstream oligomerization process as above described ("Refinery BDH"), to competitively replace new or existing acid alkylation processes in refineries. Both of the prior art HF and $H_2SO_4$-catalyzed Alkylation processes convert isobutane and butenes and/or propylene to make liquid "alkylate", a valuable low aromatic high octane gasoline blending stream. HF and $H_2SO_4$ are both strong acids, and their utilization as catalysts in a refinery process plant constitutes a significant hazard. Acid utilization and "regeneration" requires the utilization of a significant quantity of process plant and equipment, which is expensive to both install and operate. The transport of these strong acids to the refinery is in itself a significant hazard, as many refineries are situated close to commercial and residential environments.

A refinery which has a fluid catalytic cracker (FCC) may be furnished with an associated Unsaturates Gas Plant (UGP). This gas plant takes FCC main fractionator overhead vapour at low pressure—normally between one-half and three atmospheres above atmospheric pressure—and then repeatedly compresses and cools it, thereby separating it into various gaseous (non-condensable, hydrogen, methane and ethane-containing "offgas") and liquid product streams, which may include a propylene-rich stream (often called "refinery propylene"), propane and normal butane/isobutene/butenes-rich streams and/or a combined LPG ("liquid petroleum gas") product, and gasoline blending stock naphthas.

Thus, if a refinery has an FCC and its associated UGP, then the Refinery BDH plant's product may not need to be separately compressed and purified, merely to be introduced into the UGP at an appropriate position in the UGP flowscheme.

The Total Installed Capital cost of an integrated Refinery BDH plant is about MM$20-30 (20 to 30 million US Dollars) for the BDH reaction section, depending on unit capacity, plus a similar amount for an oligomerisation unit, inserted as above into an existing refinery fluid catalytic cracking (FCC) unit's unsaturates gas plant (UGP) and alkylation unit feed preparation system flowscheme; around MM$50-70 in all, depending on unit capacity.

If a refinery has no FCC nor UGP, then the integrated Refinery BDH plant's product still does not need to be separately compressed and purified, merely to be introduced into the crude distillation unit (CDU) overheads recovery gas plant ("saturates gas plant", SGP) at an appropriate position in the CDU/SGP flowscheme. In such a case, the Capital cost of a Refinery BDH integrated dehydrogenated and oligomerization plant is also around MM$50-70. This would represent a refinery with a hydrocracker (HDC) and no FCC, which refinery scheme is aimed at maximizing diesel make. This TIC figure is also probably a reasonable budget-level estimate for greenfields installations, and also for a condensate processing plant.

An $H_2SO_4$ acid alkylation unit of similar capacity, inclusive of its required feed preparation and acid regeneration equipment, may cost in the region of MM$100-150. HF acid plants involve very similar costs, but the hazards associated with acid storage and handling are often judged too dangerous by refiners to contemplate installation of a new HF acid alkylation plant. Acid alkylation plants are subject to high maintenance costs associated with high corrosion rates in both the acid reaction and regeneration sections—and also in downstream product purification plant and equipment—due to the effect of strong acids on piping, vessels, valves and other equipment.

The process arrangement of the invention may utilize only the reaction section of the dehydrogenation process. It may or may not include an Oxydehydrogenation reactor step, depending upon the value the refiner places on the hydrogen—and the cost of oxygen—that is otherwise consumed in this reaction step, in which oxygen and hydrogen are reacted together in order to decrease the hydrogen concentration in the reaction product, thereby shifting the butane/propane dehydrogenation reaction equilibrium further towards butene/propylene generation. It also may or may not require the raw gas product to be compressed, depending upon the requirements of the downstream oligomerization plant. Careful selection of such downstream oligomerization plant process technology may obviate the need for compression.

Dispensing with the process hardware associated with raw gas compression, gas separation and fractionation provides an opportunity for the total installed capital cost of the plant to be reduced, by as much as 50%.

Dispensing with an Oxydehydrogenation reactor provides an opportunity for the Total Installed Capital cost of the simplified plant to be further reduced, by as much as another 10%.

Integration of the above light paraffin dehydrogenation and oligomerization processes with each other—and with the other processing units of the plant—provides an opportunity for reducing both TIC and Operating costs via process simplification, resulting in the avoidance of the need for separate butane and butenes separation (i.e. investment in and operation of a C4 splitter). Integration of these two processes results in the consumption of the olefin, reactive in the downstream oligomerization process, from the combined paraffin and olefin product of the upstream dehydrogenation process, leaving a more concentrated paraffin stream for recycle back to the upstream unit, where it is converted into olefin.

Thus, the opportunity for avoiding capital expenditure on acid alkylation via installation of an integrated butane dehydrogenation and downstream oligomerization unit may be a saving of between MM$50 and MM80 depending on plant capacity, and operating costs may be similarly reduced by a few million Dollars annually.

BRIEF DESCRIPTION OF THE DRAWINGS

An embodiment of the process arrangement of the invention is described below by way of example only. The embodiment is a condensate processing and LPG conversion facility to manufacture high quality transport fuels meeting oil industry fuel quality standards. The embodiment is illustrated in the accompanying drawings, of which.

DETAILED DESCRIPTION OF THE INVENTION

With reference to the Figures, the embodiment of the process arrangement of the invention in the form of a condensate processing and LPG conversion facility shown in the Figures comprises the following process units:

1. Condensate Distillation (CDU),
2. Saturates Gas Processing (SGP),
3. Naphtha Pre-treatment (NHT),
4. Continuous Catalytic Reforming (CCR),
5. Combined Kerosene and Diesel Distillate Hydrotreating (DHT),
6. Light Naphtha Isomerisation (ISO),
7. Light Paraffins (Butane) Dehydrogenation (BDH), integrated with Olefins Oligomerisation (PN),
8. Benzene Alkylation (BAU), integrated with the CCR.

The above process arrangement is designed to be constructed, commissioned and operated together with the infrastructure (offsite and utility facilities) required to support the operation of the process arrangement.

A high level of integration is designed into the process arrangement, specifically with respect to (a) the heat and process integration of the CDU with the NHT and DHT, (b) the integration of the SGP with BDH feed processing, (c) integration of the BDH product purification and PN reaction sections, (d) integration of PN product stabilisation and BDH feed processing, and (e) the integration of CCR product stabilization and the BAU.

The process arrangement provides an opportunity to enable gasoline to be manufactured with benzene and aromatics content below industry specification limits at an overall gasoline pool octane of 95.3 or higher, with 94RONC CCR reformate—which contains some 65% aromatics—now comprising under 64% of the motor gasoline pool.

Should future gasoline grade demand require a higher gasoline pool octane, the process arrangement is flexible and provides an opportunity to perform as economically attractively as at its design point; the attendant increase in plant netback prices for higher octane gasoline grades will offset the incremental cost of their manufacture. This may be achieved by (a) running a marginally higher severity on the CCR, and (b) running the incremental C3 and C4 LPG produced in the CCR through the BDH and Oligomerization units to make more high octane iso-octene-rich oligomer, thus balancing the marginally increased aromatics content of the motor gasoline pool.

The unit operations of the process arrangement are described further below with reference to the Figures.

Figure 1:
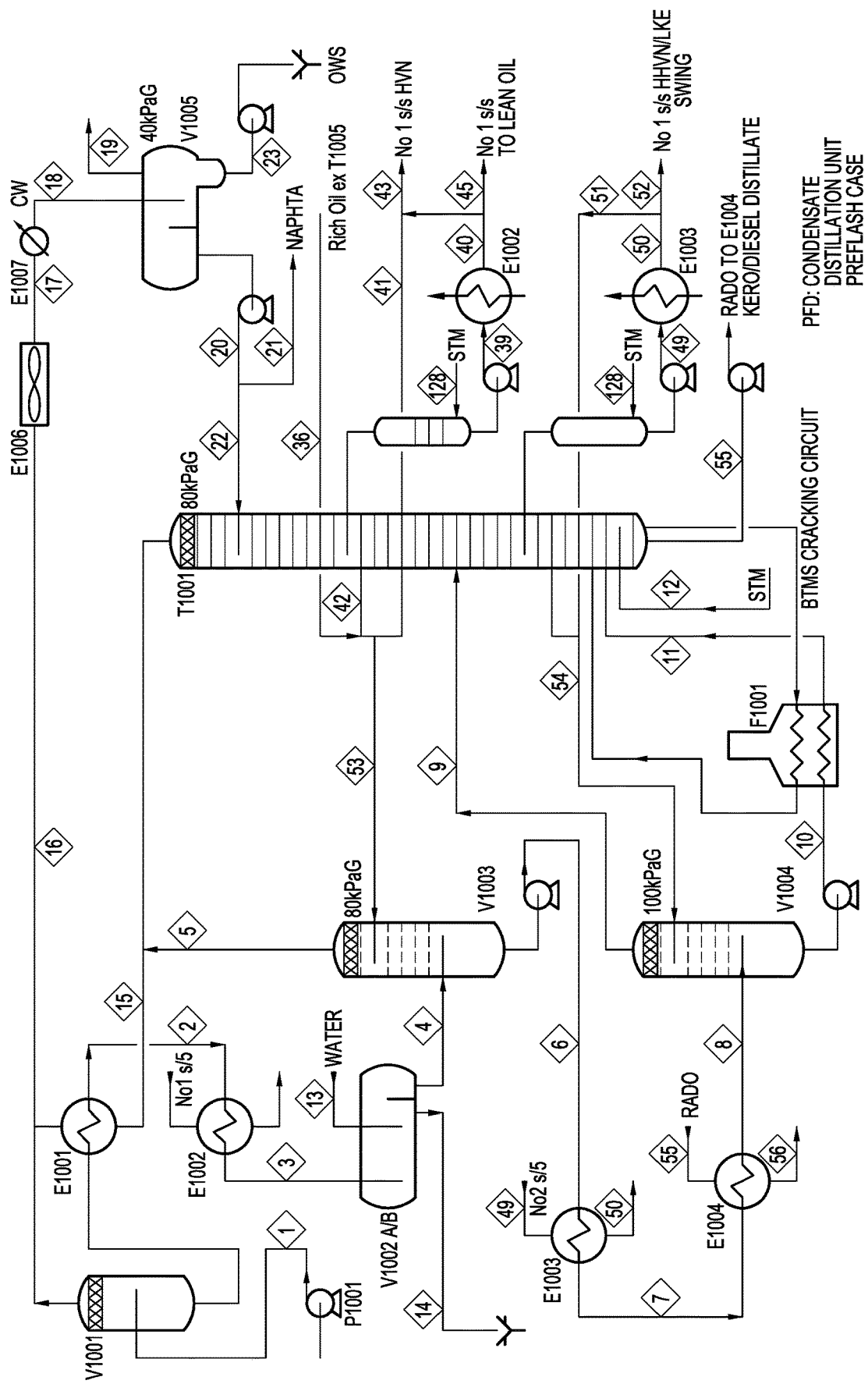
FIG. 1 is a flowsheet of the condensation distillation unit of the embodiment of the process arrangement.

With reference to FIG. 1, for simplicity, hot bypass on No1 sidestream (s/s, stream 43) to the NHT is not shown. Also, air coolers are not shown on all side-draw and bottoms product streams. Process simplification of the CDU via process and heat integration with DHT is shown, as RADO stream 55 is routed directly to DHT (not shown) without cooling. It may prove possible to dispense with the No2 sidestream draw, depending on detailed column simulation.

The Naphtha Processing Units include: Naphtha Hydtrotreater (NHT), Light Naphtha Isomerisation (ISO), Continuous Catalytic Reformer (CCR), and Benzene Alkylation Unit (BAU)—process licensor ExxonMobil's process name "Benzout"

Detailed flow diagram elements are not shown in FIG. 1. Option (1) co-isomerizes n-butanes to isobutane in ISOM reactor.

The Light Ends Processing Units include: Butane Dehydrogenation Unit (BDH) and Olefins Oligomerisation Unit (PN).

1. Condensate Supply

Condensate is supplied to the plant by pipeline from vessel receiving facilities and storage facility.

2. Condensate Distillation Unit (CDU) and Saturates Gas Plant (SGP)—See FIG. 1

Condensate is pumped from the condensate storage tanks to the Condensate Distillation Unit (CDU) for separation into incondensible (C2-) gases, mixed C3/C4 LPG, full-range C5+ virgin naphtha (FVN) and raw distillate (RAD) streams. An electrostatic desalter is positioned partway along the CDU preheat heat exchanger train, at a point where condensate temperature achieves approximately 100 C. Desalter water is routed to plant effluent water treatment facilities.

Warm condensate from the desalter is pumped through the rest of the CDU preheat train to the CDU heater and thence to the condensate distillation tower. This is a complex distillation tower with sidestreams and pump around heat exchange facilities to enable the production of the above-mentioned product streams. The tower top pressure should be minimised, running as close to 100 KPaG as possible.

CDU tower overheads are routed through a cold condensate preheat cooler to an air condenser and then to a trim water cooler and then to the CDU overheads accumulator at a temperature of 40° C. The CDU overheads compressor takes suction on the vapour space of this large vessel at around 80 KPaG, and increases the overhead vapour stream pressure to around 1500 KPaG. The hot compressed vapour flows through another condensate preheat heat exchanger and/or an air-cooled cooler and water trim cooler to again reduce temperature to 40° C., and thence to the CDU SGP absorber de-ethaniser. C3 and C4 (propane and mixed butanes, LPG) are absorbed by a lean oil supplied to this tower, while C2-gas (ethane and lighter gases) from this column's overhead system is routed to the plant's fuel gas supply system; the column's C3/C4 side-draw product vapour is routed via an aircooled condenser and water trim cooler to the CDU overhead product receiver, and thence either to LPG storage or to the Naphtha Pretreater (NHT) together with full range virgin naphtha.

Full range virgin naphtha (FVN, No 1 sidestream) is drawn from the CDU tower as a liquid side-draw into the No 1 sidestream stripper, stripped using LPG or steam, cooled against condensate and either pumped back to the tower (top pumparound), or routed directly to the DCF Naphtha Pretreater (NHT), or further cooled in an air cooler and water trim cooler for rundown to storage.

Raw Distillate CDU tower bottoms (RAD) is taken from the CDU tower as a liquid and cooled against incoming cold condensate, and either pumped back to the tower (bottoms pumparound), or directly to the Distillate Hydrotreater (DHT), or further cooled in an air cooler and water trim cooler to 40° C. for rundown to storage.

Figure 2:
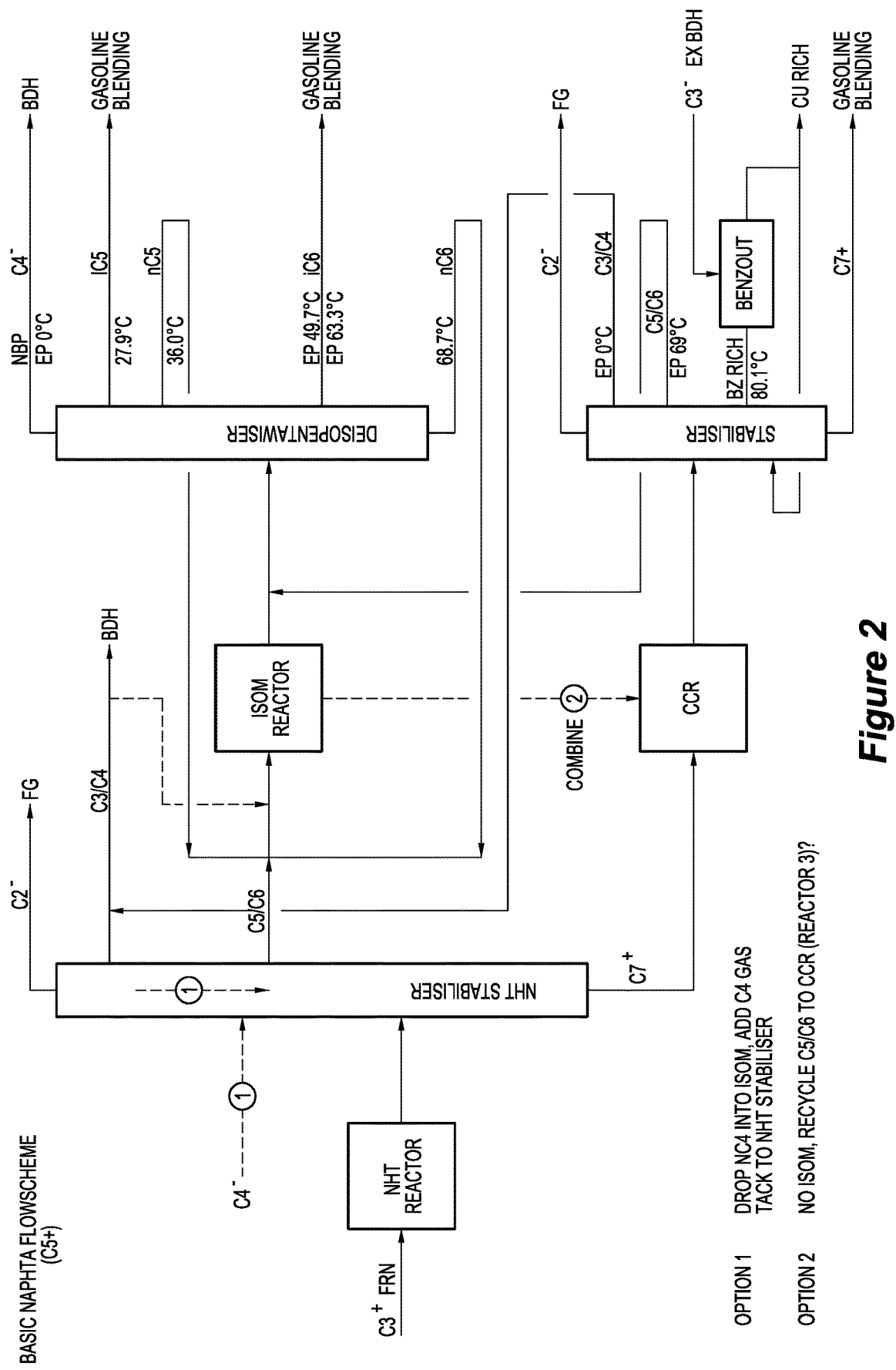
FIG. 2 is a flowsheet of the light ends processing units of the embodiment of the process arrangement.

3. Naphtha Hydrotreater (NHT)—See FIG. 2

During normal operation, mixed C3/C4 LPG from the CDU overheads system, along with hot stripped No1 sidestream (Full Virgin naphtha, FVN) from the CDU, is taken directly to the Naphtha Hydrotreater (NHT) after heat exchange in the condensate preheat train of the CDU. This heat integration of the two process units maximises energy savings, as FVN and LPG is otherwise cooled and stored and then drawn at ambient temperature from FVN and LPG tankage.

During start-up and/or shut-down operations however, FVN and LPG are cooled and routed to tankage.

The naphtha pretreater reduces the sulphur content of the mixed C3/C4 LPG and FVN to low ppb levels ("parts per billion") in order to avoid poisoning of the downstream CCR, Isomerisation and Dehydrogenation Unit catalysts.

The reaction section of the NHT includes feed/effluent heat exchange, a fired process heater, mixing with hydrogen-rich gas from the CCR, and the NHT reactor itself, which includes a fixed bed of Cobalt-Molybdenum catalyst in which any sulphur compounds present in the feedstocks react with the circulating hydrogen to form gaseous hydrogen sulphide ($H_2S$). After cooling in the feed/effluent exchanger, the reaction product is condensed and fed to a high pressure flash vessel where hydrogen is recovered for recirculation. The treated naphtha is then fed to the NHT Stabiliser, where non-condensing C2-offgas is taken to the fuel gas system and a mixed C3/C4 LPG stream is taken as an overhead liquid. $H_2S$ is absorbed from these two streams by contacting with a weak liquid amine solution. A gas/steam-stripped liquid side-draw of C5 light naphtha (LN) is taken hot directly to the Isomerisation Unit. The NHT stabiliser bottoms C6+ naphtha is normally fed directly to the CCR. Cooled C6+ naphtha can be taken to/through storage, where a two-day stock for start-up purposes is always held.

4. Continuous Catalytic Reformer (CCR)—FIG. 2

The hot pretreated C6+ naphtha from the NHT is fed to the reaction section of the Continuous Catalytic Reformer (CCR), which consists of feed/effluent heat exchange, followed by a succession of fired process heaters and reactors containing a noble metal-promoted (usually Pt—Re, Platinum/Rhenium) catalyst. Isomerisation, dehydrogenation, and cyclisation (aromatisation) reactions occur, releasing hydrogen-rich gas and increasing product RONC. After cooling in the feed/effluent exchanger, the reaction product is condensed and fed to a high pressure flash vessel where hydrogen is recovered for recirculation and for supply to the NHT.

The full range "reformate" product is then fed to the CCR product stabilizer column, where non-condensing C2-offgas is taken to the fuel gas system and a mixed C3/C4 LPG stream is taken as an overhead liquid. A steam-stripped liquid side-draw of C5/C6 light reformate (LR) is taken hot directly to the Isomerisation Unit. A gas-stripped (preferable) or steam-stripped benzene-rich liquid side-draw is taken hot directly to the Benzene Alkylation Unit (BAU), where benzene in this stream is alkylated with propylene from the BDH unit, and cumene-rich reaction product may be returned directly to the CCR product stabiliser. The CCR stabiliser bottoms C7+ reformate is cooled and sent to gasoline blending and storage.

5. Isomerisation (ISO)—See FIG. 2

The pentane side-draw from the NHT stabiliser, along with the pentane/hexane rich light reformate side-draw from the CCR stabiliser is fed to the Isomerisation Unit reaction section. This consists of feed/effluent heat exchange, a fired process heater, mixing with hydrogen-rich gas from the CCR, and the ISOM reactor itself, which includes a fixed bed of platinum-based catalyst in which normal paraffinic molecules present in the feedstock are converted to the corresponding iso-paraffin. The process conditions in the ISOM reactor favour an equilibrium composition consisting of approximately 60% iso- and 40% n-paraffins.

After cooling in the feed/effluent exchanger, the reaction product is condensed and fed to a high pressure flash vessel where hydrogen is recovered for recirculation. The liquid product is then fed to the Deisopentaniser, where any C4-offgas is taken to the BDH Unit, and an isopentane-rich stream (iC5) is taken as an overhead liquid product for gasoline blending. A gas-stripped liquid side-draw of normal pentane (NC5) is taken hot and recycled back to the Isomerisation Unit feed surge drum. A gas-stripped or steam-stripped liquid side-draw of iso-hexanes (iC6) is cooled and sent to storage for gasoline blending. The NHT stabiliser bottoms nC6-rich material is also recycled back to the Isomerisation Unit feed surge drum.

The co-isomerisation of normal butane to isobutene in this process unit, in order to enable octane-boosting increased iso-octene production in the Oligomerisation unit, and further reduction of CCR operating severity, may prove economically beneficial in very high gasoline pool octane demand scenarios.

Installation of an additional distillation column, to separate isobutene feed for the BDH unit from all the n-butane in the mixed C4 ISOM product stream, which are then recycled back to the ISOM, will further concentrate isobutene in the BDH unit feed. In this scenario, maximum iso-octene production in the Oligomerisation unit is achieved, and still further reduction of CCR operating severity. This may prove economically beneficial in extremely high gasoline pool octane demand scenarios.

6. Benzene Alkylation (BAU)—See FIG. 2

A gas-stripped (preferable) or steam-stripped benzene-rich liquid side-draw is taken directly from the CCR product stabilizer to the Benzene Alkylation Unit (BAU) reactor, where benzene in this stream is alkylated with a mixed propane/propylene stream from the BDH unit over a zeolite-based catalyst. Benzene alkylation takes place at moderate temperature and pressure conditions with an excess of benzene: all propylene supplied to the BAU reactor is consumed.

Unreacted benzene and all propane is returned to the CCR product stabilizer, while High Octane cumene-rich reaction product may either be also returned directly to the CCR product stabilizer, or alternatively it may be separated from the unreacted benzene and sent to segregated storage, whence it may be used for both motor and aviation gasoline blending.

Figure 3:
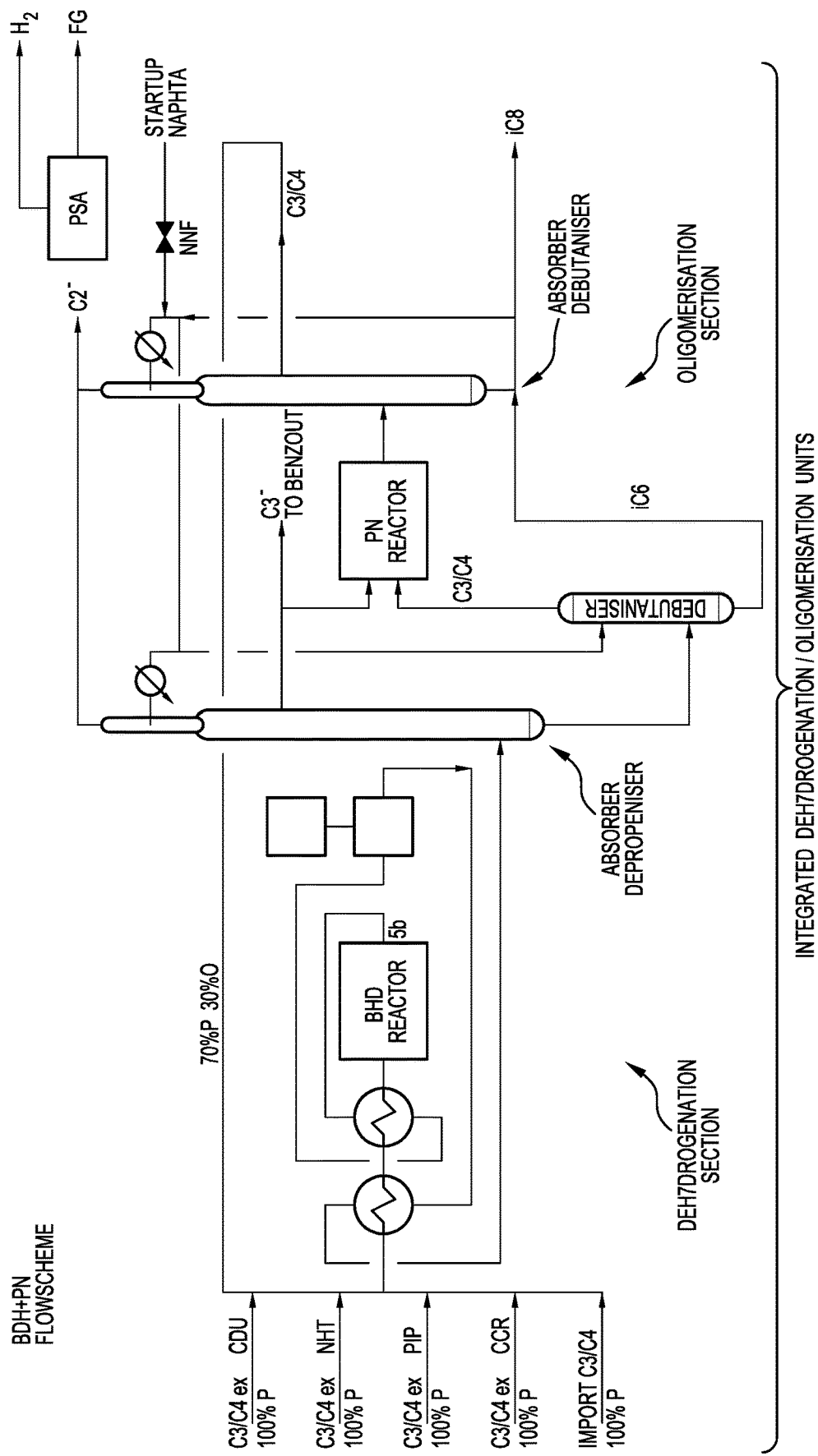
FIG. 3 is a flowsheet of the Butane Dehydrogenation and Oligomerisation units of the embodiment of the process arrangement.

7. Butane Dehydrogenation (BDH)—See FIG. 3

Mixed C3/C4 LPG streams are collected from the CDU, the NHT stabiliser, the ISOM Deisopentaniser, the CCR stabiliser and import C3/C4 LPG tankage, and are fed through feed/effluent exchange and fired process heating to the BDH reactor, where they are dehydrogenated at high temperature (+/−600° C.) by exposure to a Ni or zeolite-based catalyst. The BDH reactor product, containing around 60% olefins (propylene at least sufficient to satisfy BAU requirements for benzene alkylation, and—mainly—mixed iso and n-butenes) at around 500 KPaG pressure, is cooled, compressed to around 1750 KPaG, and then cooled again against cold reactor feed. It is then fed to an Absorber-Depropeniser, from which C2-incondensable gases are removed and routed to a rapid cycle PSA (pressure swing absorption) plant or alternative plant for recovery of hydrogen, and thence to fuel gas.

A lean ("sponge") oil, comprising of iso-octane rich naphtha from the Oligomerisation Unit (PN) is supplied to the top of the absorber section of this tower, which operates at around 1620 KPaG and 40 C. A liquid propylene-rich side-draw is taken from the top of the lower rectification section of this tower as feed for the benzene alkylation unit (BAU), while the C3/nC4/iC4/nc4=/iC4=/iC8 containing bottoms product is routed to a debutaniser, which is also supplied with iC8-rich lean oil recycle to the top tray.

The 40/60 paraffin/olefin butene-rich debutaniser overhead product is fed, along with surplus propylene, to the Oligomerisation Unit (PN), where the olefins oligomerise to form a mixture of N-octene (NC8) and iso-octenes (iC8), with an octane rating of around 100-103 RONC.

8. Oligomerisation (PN)—See FIG. 3

Propylene surplus to BAU requirements, along with the C3/nC4/iC4/nc4=/iC4=overhead product from the BDH debutaniser, is fed to a light olefin oligomerisation unit, where olefins contained in the above streams are dimerised to form an iso-octene rich liquid product. This is fed to an Absorber-Debutaniser (very similar to the Absorber-Depropeniser of the BDH unit), where C2-incondensable gases are removed and routed to the same PSA (pressure swing absorption) plant or alternative plant for recovery of hydrogen, and thence to fuel gas. A lean ("sponge") oil, comprising of iso-octane rich naphtha from the Absorber-Debutaniser bottoms stream is supplied to the top of the absorber section of this tower, which operates at around 1620 KPaG and 40 C.

A mixed C3/C4 side-draw is taken as recycle to the feed surge drum of the Butane Dehydrogenation (BDH) unit, while the stabilised 100-103 RONC iC8-rich bottoms oligomer product is routed to storage and gasoline blending. This C3/C4 recycle stream has the effect of integrating the BDH and PN units, enabling the PN unit to effectively provide this paraffin-rich stream to boost the feed paraffin content of the BDH unit.

The above-described embodiment of the process arrangement of the invention provides an opportunity to achieve a very high transport fuels manufacturing margin due to the choice of chemical processes utilized, the high level of integration of unit operations, and the process simplification thereby achieved.

The above-described embodiment of the process arrangement of the invention provides an opportunity to an increase in net manufacturing margin of 100% above that achieved by using the traditional oil industry prior art processing scheme.

In addition, the above-described embodiment of the process arrangement of the invention provides an opportunity to minimise the Total Installed Capital Cost (TIC) of facilities required to manufacture high specification gasoline and distillate transport fuels due to the high level of integration of unit operations, and the resultant process simplification.

The high level, of integration in the above-described embodiment of the process arrangement of the invention provides an opportunity to achieve significant capital expenditure reductions and resultant TIC savings of between MM$100 and MM$150 for a 65,000 barrel/day condensate and butane processing scheme.

Many modifications may be made to the embodiment of the method and the apparatus of the present invention shown in the drawings without departing from the spirit and scope of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

What is claimed is:

1. A process for producing transport fuel blendstocks, the process comprising:
   providing a first feedstock comprising butane and propane, and a second feedstock comprising benzene;
   dehydrogenating the first feedstock in a first reactor to produce a C4 product comprising butane and butene and a C3 product comprising propane and propylene;
   splitting, via a C3/C4 splitter, the C4 product from the C3 product that are produced in the first reactor;
   oligomerizing the C4 product in a second reactor to produce a first transport fuel blendstock; and
   alkylating the C3 product with the second feedstock in a third reactor to produce a second transport fuel blendstock.

2. A process as claimed in claim 1 also comprising recovering butane from an output of the second reactor and transferring the butane to the first reactor.

3. A process as claimed in claim 1 also comprising recovering propane from an output of the third reactor and transferring the propane to the first reactor.

4. A process as claimed in claim 1 also comprising obtaining the second feedstock from catalytically reformed naphtha.

5. A process as claimed in claim 4 also comprising obtaining the second feedstock as a benzene rich side stream from a stabilizer column of a catalytically reformed naphtha process unit.

6. A process as claimed in claim 5 also comprising recovering any one or more of propane, propylene or benzene from an output of the third reactor and transferring the propane, propylene and/or benzene to the stabilizer column of the catalytically reformed naphtha process unit.

7. A process as claimed in claim 6 also comprising recovering the propane and propylene in an output from the stabilizer column and transferring the recovered propane and propylene to the first reactor.

8. A process as claimed in claim 5 also comprising outputting a third transport fuel blendstock from the stabilizer column of the catalytically reformed naphtha process unit for blending on site.

9. A process as claimed in claim 5 also comprising returning all of the output of the third reactor to the stabilizer column of the catalytically naphtha reforming process unit.

10. A system for producing transport fuel blendstocks, the system comprising:
    a first reactor that dehydrogenates a first feedstock comprising butane and propane to produce a C4 product comprising butane and butene and a C3 product comprising propane and propylene;
    a C3/C4 splitter that splits the C4 product from the C3 product that are produced in the first reactor;
    a second reactor that oligomerizes the C4 product in a second reactor to produce a first transport fuel blendstock; and
    a third reactor that alkylates the C3 product with a second feedstock comprising benzene in a third reactor to produce a second transport fuel blendstock.

11. A system as claimed in claim 10 also comprising a separator that recovers butane from an output of the second reactor and transferring the butane to the first reactor.

12. A system as claimed in claim 10 also comprising a stabilizer column arranged to receive a catalytically reformed naphtha and to produce the second feedstock as a benzene rich side stream.

13. A system as claimed in claim 12 also comprising a separator that recovers any one or more of propane, propylene or benzene from an output of the third reactor that transfers the propane, propylene and/or benzene to the stabilizer column.

14. A transport fuel comprising a blendstock produced by the process as claimed in claim 1.

15. A transport fuel comprising a blendstock produced using the system as claimed in claim 10.

* * * * *